United States Patent [19]

Blasius, Jr.

[11] Patent Number: 4,767,398

[45] Date of Patent: Aug. 30, 1988

[54] SWAB APPLICATOR COMPRISING A FLOCK SWAB TIP

[75] Inventor: William G. Blasius, Jr., Higganum, Conn.

[73] Assignee: Chesebrough-Pond's Inc., Greenwich, Conn.

[21] Appl. No.: 855,669

[22] Filed: Apr. 25, 1986

[51] Int. Cl.⁴ .............................................. P61F 2/06
[52] U.S. Cl. ................................................... 604/1
[58] Field of Search ...................... 132/88.7; 604/2, 1; 15/210 R

[56] References Cited

U.S. PATENT DOCUMENTS

| | | | |
|---|---|---|---|
| 1,816,108 | 7/1931 | Blumenfeld | 15/244 |
| 3,443,562 | 5/1969 | Gustafson | 604/1 |
| 4,404,977 | 9/1983 | Vasas | 132/88.7 |

Primary Examiner—Robert Peshock
Attorney, Agent, or Firm—Melvin H. Kurtz

[57] ABSTRACT

An applicator comprising a support stick having mounted on at least one end thereof a one-piece swab formed of a fibrous, non-woven material having an outer flock surface is described. The applicator is useful in the application of such cosmetics as eye shadow and eye liner.

8 Claims, 1 Drawing Sheet

SWAB APPLICATOR COMPRISING A FLOCK SWAB TIP

BACKGROUND OF THE PRESENT INVENTION

1. Field of the Invention

The present invention relates to a swab applicator having a swab tip member with an outer flock surface.

2. Description of the Prior Art

U.S. Pat. No. 3,863,654 to B. P. Morane et al. describes a cosmetic applicator which, in one embodiment, can comprise a stick having flock fibers attached to its end by means of a suitable adhesive. The flock fibers are viewed as alternative supporting means for a cosmetic with either woven or non-woven cotton fibers being described as an alternative supporting medium (see Col. 1, lines 41–50). Clearly, this patent does not show or suggest the conjunctive use of a swab tip and a flock surface.

Swab applicators comprising a support stick carrying at least one swab tip are well known. For example, U.S. Pat. No. 3,871,375 to R. A. Bennett illustrates a double-ended swab formed of resilient polymer foam material which terminates in soft, porous, ellipsoidal ends with open cavities. U.S. Pat. No. 3,586,380 to G. Alibeckoff illustrates a swab comprising a stick having a teardrop-shaped non-woven mass of cotton fibers at one end thereof covered by an adherent sheath of regenerated cellulose sponge.

Applicators for cosmetics comprising a support stick terminating in a swab having an outer flock surface are known. Such applicators have a two-piece swab tip member formed by bonding together two pieces of polyurethane foam. The swab tip is somewhat paddle-shaped and has a flock, fibrous outer surface formed by bonding flock fibers adhesively to the paddle-shaped, two piece polyurethane foam swab member. Such applicators have several problems associated with them. The first is their tendency to delaminate by separation of the two pieces of polyurethane foam which formed the nucleus of the swab member. Such applicators are relatively expensive to manufacture since the bonding of the polyurethane foam to form the paddle-shaped swab tip is relatively time consuming. Also, the polyurethane foam which comprises the two-part swab tip is often subject to ultraviolet light degradation.

SUMMARY OF THE PRESENT INVENTION

The applicator of the present invention is an improvement over the last aforementioned applicator in regard to its cost of construction and its durability. The present applicator comprises a support stick having mounted on at least one end thereof a one-piece swab formed of a fibrous non-woven material which has an outer flock surface. The use of such a non-woven fibrous material in a one-piece construction overcomes the problems of delamination attendant with the prior art applicator since the present applicator has no bond lines in its swab member which can delaminate. Also, the applicator of the present invention is much less costly to manufacture than an applicator that is formed by bonding together two foam members to make the swab tip component. It can thus yield a disposable, low cost, single use product which will be more sanitary than applicators in current usage.

As compared to a normal cotton swab not containing the flock outer surface of the present invention, the applicator of the present invention has certain additional advantages. The flocked applicator exhibits better pick up and release qualities in regard to many substances than does a normal cotton swab. The perpendicular fibers of the flocked applicator offer no edges or crevices for such compositions as makeup to be trapped within unlike the lateral orientation of a conventional cotton swab fiber body. This quality also allows the present applicators to more uniformly apply a composition such as makeup, with less streaking and to more effectively allow for blending procedures. Persons who use the applicator in the eye region may also notice a much lessened tendency for stray fibers to enter the eye since the adhesive used to bond the flock fibers to the swab keeps the swab fibers more permanently and firmly bound.

DESCRIPTION OF THE DRAWINGS

The applicator of the present invention will be further understood by reference to the Drawings which form a portion of the present specification wherein.

DETAILED DESCRIPTION OF THE PRESENT INVENTION

Figure 1:
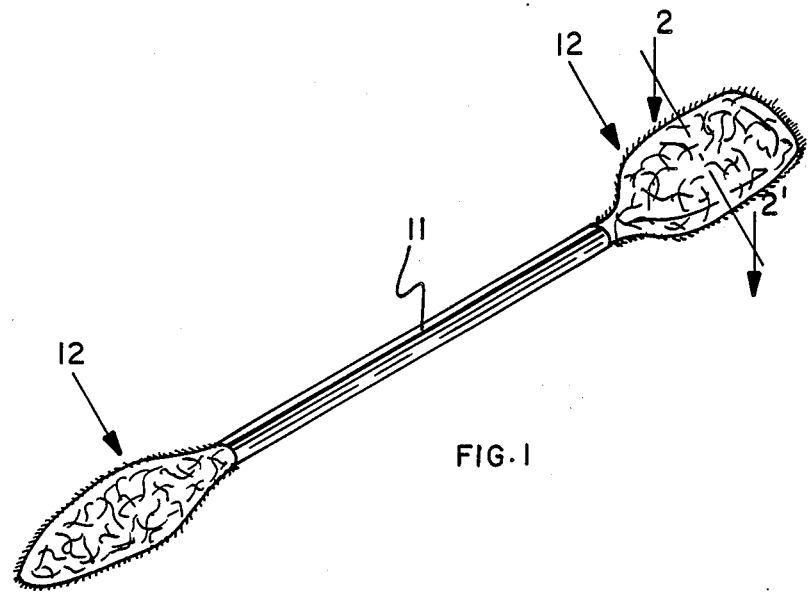
FIG. 1 is a perspective view showing a preferred embodiment of the present invention.

The swab applicator of the present invention, in a preferred embodiment, is shown in FIG. 1. It comprises an applicator stick 11 which has mounted on at least one end thereof a suitable swab member 12 in accordance with the present invention. The drawing illustrates the swab applicator of the present invention which has a paddle-shaped applicator at one end and a cone-shaped applicator at the other. Obviously, the present invention is not limited to such a configuration and can, if desired, have either one or two swab members of either the same or differing shape.

Figure 2:
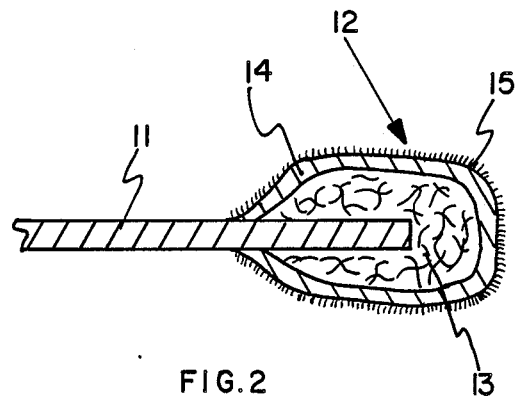
FIG. 2 is a cross-sectional view taken along the lines of 2—2' of FIG. 1 showing one swab member of the present invention.

FIG. 2 shows the swab member in greater detail. It comprises the underlying one-piece swab 13 formed of a fibrous, non-woven material (either natural or synthetic fibers or blends thereof) as is conventionally known to a person of ordinary skill in the art. Overlying the material 13 is a layer of suitable adhesive 14 having a plurality of flock fibers 15 on its outermost surface. Such a configuration produces the desired one-piece swab formed of a fibrous, non-woven material having the desired outer flock surface.

In the preferred embodiment the applicator is produced by the following process. The first step involves winding a blend of cotton and synthetic fibers onto the end of the applicator stick 11 as is conventionally known in the art. The applicator stick can be formed of plastic if desired. Other materials, such as paper and wood, can also be used to form the stick 11. In a preferred embodiment, one blend of the fibers is formed into the shape of a cone, whereas the other is first formed into the shape of a sphere and pressed into a paddle-like shape. The next step involves the application of a dilute solution of a suitable adhesive to the fibers forming the underlying swab member. Preferably an acrylic, pressure-sensitive adhesive is utilized. The last step is the spraying of suitable flock fibers onto the adhesive until the outer surface of the swab has been completely covered. Synthetic fibers of from about 1 to about 1.5 denier and from about 0.25 to about 0.35 inch in length have been found to be suitable.

The foregoing illustrates certain embodiments of the present invention but should not be construed in a limiting sense. The scope of protection that is desired is set forth in the claims which follow.

What is claimed is:

1. A swab applicator comprising an applicator stick having mounted on at least one end thereof a one-piece swab formed of a fibrous non-woven material having an outer flock surface.

2. An applicator as claimed in claim 1 wherein the flock outer surface is adhesively bonded to a non-woven swab material.

3. An applicator as claimed in claim 1 wherein the non-woven material comprises cotton.

4. An applicator as claimed in claim 2 wherein the non-woven material comprises a blend of cotton and synthetic fibers.

5. An applicator as claimed in claim 1 wherein the applicator stick is formed of plastic.

6. An applicator as claimed in claim 4 wherein the applicator stick is formed of plastic.

7. An applicator as claimed in claim 2 wherein the adhesive is a pressure sensitive adhesive.

8. An applicator as claimed in claim 6 wherein the adhesive is a pressure sensitive adhesive.

* * * * *